United States Patent
Dijksman et al.

(10) Patent No.: US 8,597,279 B2
(45) Date of Patent: Dec. 3, 2013

(54) SWALLOWABLE MULTI-NOZZLE DOSING DEVICE FOR RELEASING MEDICINES IN THE GASTROINTESTINAL TRACT

(75) Inventors: Johan Frederik Dijksman, Weert (NL); Anke Pierik, Eindhoven (NL); Judith Margreet Rensen, Eindhoven (NL); Jeff Shimizu, Cortlandt Manor, NY (US); Hans Zou, Windsor, NJ (US); Ivar Schram, Weert (NL)

(73) Assignee: Medimetrics Personalized Drug Delivery, Inc., Briarcliff Manor, NY (US)

( * ) Notice: Subject to any disclaimer, the term of this patent is extended or adjusted under 35 U.S.C. 154(b) by 352 days.

(21) Appl. No.: 12/447,808

(22) PCT Filed: Oct. 17, 2007

(86) PCT No.: PCT/IB2007/054223
§ 371 (c)(1),
(2), (4) Date: Apr. 29, 2009

(87) PCT Pub. No.: WO2008/053396
PCT Pub. Date: May 8, 2008

(65) Prior Publication Data
US 2010/0049120 A1     Feb. 25, 2010

Related U.S. Application Data

(60) Provisional application No. 60/863,649, filed on Oct. 31, 2006.

(51) Int. Cl.
*A61K 9/22* (2006.01)
*A61M 31/00* (2006.01)
*A61K 9/52* (2006.01)

(52) U.S. Cl.
USPC ........................ 604/890.1; 604/67; 424/457

(58) Field of Classification Search
USPC ......... 604/66, 67, 890.1, 891.1; 424/451, 457
See application file for complete search history.

(56) References Cited

U.S. PATENT DOCUMENTS 4,239,040 A * 12/1980 Hosoya et al. ................ 604/135
(Continued)

FOREIGN PATENT DOCUMENTS

WO    2006021932 A1    3/2006
WO    2006025013 A1    3/2006
(Continued)

OTHER PUBLICATIONS

Japanse Office Action mailed Jun. 4, 2013 for Japanese patent application No. 2009-533999, a counterpart foreign application of U.S. Appl. No. 12/447,808, 6 pages.

*Primary Examiner* — Victoria P Shumate
(74) *Attorney, Agent, or Firm* — Lee & Hayes, PLLC

(57) ABSTRACT

A capsule and methodology for dispensing a medicament in the gastrointestinal tract of a mammal is disclosed, the gastrointestinal tract having tissue sites of interest. The capsule may include a medicament reservoir; medicament dispensing means such as a plurality of piezoelectric droplet jet nozzle dispensers; a power source; electronic control circuitry means and/or detecting means capable of communicating with a medicament dispensing means for regulating the amount and time interval for dispensing of the medicament into the gastrointestinal tract by the medicament dispensing means; and a non-digestible outer protective shell housing, e.g., the medicament reservoir, medicament dispensing means and electronic control circuitry means. A plurality of the nozzle dispensers of the medicament dispensing means can be positioned tangentially to a surface of the housing such that during release of a medicament, the capsule is caused to rotate and/or translate so as to discharge the medicament homogeneously onto tissue sites of interest. In addition, by using multiple nozzles and releasing medicament at high speed, this facilitates medicament absorption by the intestines in the gastrointestinal tract.

23 Claims, 4 Drawing Sheets

(56) References Cited

U.S. PATENT DOCUMENTS

| | | | |
|---|---|---|---|
| 4,425,117 A * | 1/1984 | Hugemann et al. | 604/244 |
| 4,543,955 A * | 10/1985 | Schroeppel | 600/348 |
| 5,167,626 A * | 12/1992 | Casper et al. | 604/891.1 |
| 5,170,801 A * | 12/1992 | Casper et al. | 600/582 |
| 5,318,557 A | 6/1994 | Gross | |
| 5,395,366 A * | 3/1995 | D'Andrea et al. | 604/890.1 |
| 5,558,640 A * | 9/1996 | Pfeiler et al. | 604/67 |
| 5,728,396 A * | 3/1998 | Peery et al. | 424/422 |
| 6,929,636 B1 | 8/2005 | Alten | |
| 7,118,531 B2 * | 10/2006 | Krill | 600/309 |
| 7,201,872 B2 * | 4/2007 | Meron | 422/404 |
| 7,282,045 B2 * | 10/2007 | Houzego et al. | 604/890.1 |
| 7,382,263 B2 * | 6/2008 | Danowski et al. | 340/572.1 |
| 7,658,736 B2 * | 2/2010 | von Alten | 604/890.1 |
| 2001/0051766 A1 * | 12/2001 | Gazdzinski | 600/309 |
| 2002/0055734 A1 * | 5/2002 | Houzego et al. | 604/891.1 |
| 2003/0191430 A1 * | 10/2003 | D'Andrea et al. | 604/66 |
| 2003/0213495 A1 * | 11/2003 | Fujita et al. | 128/899 |
| 2004/0122315 A1 * | 6/2004 | Krill | 600/437 |
| 2004/0162501 A1 * | 8/2004 | Imran | 600/547 |
| 2004/0242962 A1 * | 12/2004 | Uchiyama | 600/118 |
| 2004/0253304 A1 | 12/2004 | Gross | |
| 2005/0075559 A1 * | 4/2005 | Houzego et al. | 600/424 |
| 2005/0147559 A1 | 7/2005 | Alten | |
| 2005/0154374 A1 * | 7/2005 | Hunter et al. | 604/890.1 |
| 2005/0158246 A1 | 7/2005 | Takizawa | |
| 2006/0093663 A1 | 5/2006 | Suzuki | |
| 2007/0129703 A1 * | 6/2007 | D'Andrea et al. | 604/503 |
| 2007/0149954 A1 * | 6/2007 | Hood et al. | 604/891.1 |
| 2007/0213659 A1 * | 9/2007 | Trovato et al. | 604/67 |
| 2008/0188837 A1 * | 8/2008 | Belsky et al. | 604/890.1 |
| 2008/0269664 A1 * | 10/2008 | Trovato et al. | 604/20 |
| 2008/0275430 A1 * | 11/2008 | Belsky et al. | 604/890.1 |
| 2009/0275923 A1 * | 11/2009 | Shimizu et al. | 604/890.1 |
| 2009/0306633 A1 * | 12/2009 | Trovato et al. | 604/891.1 |
| 2010/0049120 A1 * | 2/2010 | Dijksman et al. | 604/66 |

FOREIGN PATENT DOCUMENTS

| | | |
|---|---|---|
| WO | 2006064502 A2 | 6/2006 |
| WO | 2006/077528 A2 | 7/2006 |
| WO | 2006077529 A2 | 7/2006 |
| WO | 2007057838 A1 | 5/2007 |
| WO | 2007148238 A1 | 12/2007 |
| WO | 2008012700 A1 | 1/2008 |
| WO | 2008017967 A1 | 2/2008 |
| WO | 2008038199 A1 | 4/2008 |

\* cited by examiner

SWALLOWABLE MULTI-NOZZLE DOSING DEVICE FOR RELEASING MEDICINES IN THE GASTROINTESTINAL TRACT

The present disclosure is related to U.S. Provisional Patent Application No. 60/644,540, entitled "Electronicially Controlled Capsule For Releasing Radiation", and filed Jan. 18, 2005, U.S. Provisional Patent Application No. 60/644,539, entitled "Electronicially Controlled Capsule", and filed Jan. 18, 2005, U.S. Provisional Patent Application No. 60/644,538, entitled "Electronicially Controlled Ingestible Capsule", and filed Jan. 18, 2005, U.S. Provisional Patent Application No. 60/644,518, entitled "System And Method For Controlling Traversal Of An Ingested Capsule", and filed Jan. 18, 2005, U.S. Provisional Patent Application No. 60/606,276, entitled "Electronically Controlled Pill And System For Delivering At Least One Medicament", and filed Sep. 1, 2004, U.S. Provisional Patent Application No. 60/605,364, entitled "Electronically And Remotely Controlled Pill And System For Delivering At Least One Medicament", and filed Aug. 27, 2004, U.S. Provisional Patent Application No. 60/738,238, entitled "System and Method for Interacting With a Cell or Tissue", and filed Nov. 18, 2005, U.S. Provisional Patent Application No. 60/805,223, entitled "Electronic Capsule And Method For Treating Gastrointestinal Disease", and filed Jun. 20, 2006, U.S. Provisional Patent Application No. 60/805,645, entitled "Medicament Delivery System And Process", and filed Jun. 23, 2006, U.S. Provisional Patent Application No. 60/821,622, entitled "Device, System And Method for Interacting With A Cell Or Tissue In A Body", and filed Aug. 7, 2006, and U.S. Provisional Patent Application No. 60/826,838, entitled "Medicament Delivery Apparatus", and filed Sep. 25, 2006, with each of the foregoing references being assigned to the Assignee of the present disclosure and hereby being expressly incorporated by reference as part hereof.

The disclosure is directed to an ingestible capsule for dispensing a medicament in the gastrointestinal tract of a mammal, the gastrointestinal tract having tissue sites of interest, the capsule having a medicament reservoir; medicament dispensing means including a plurality of piezoelectric droplet jet nozzle dispensers; a power source (e.g. one or more batteries); electronic control circuitry means communicating with the medicament dispensing means for regulating the amount and time interval for dispensing of the medicament into the gastrointestinal tract by the medicament dispensing means; and a non-digestible outer protective shell housing the medicament reservoir, medicament dispensing means and electronic control circuitry means. A plurality of the nozzle dispensers of the medicament dispensing means is positioned tangentially to the surface of the housing such that during discharge of the medicament, the capsule is caused to rotate and/or to translate so as to discharge the medicament homogeneously onto the tissue sites of interest. In addition, by using multiple nozzles and releasing medicament at high speed, this facilitates medicament absorption by the intestines in the gastrointestinal tract.

A medicament is generally administered as a capsule or a liquid to be taken at least one time per day. A person may be required to take or be administered several medicaments each day during the same or different times. This requires that the person or his caregiver maintain a log or remember which medicaments to take or administer at different times during the day.

A medicament, such as aspirin, taken by the person generally traverses the gastrointestinal (GI) tract where it is absorbed for treating an ailment or condition. Objects typically pass through the GI tract in 20-40 hours. Several medicaments are available as time-release capsules for releasing portions of the medicament into the body at different times (also referred to as controlled medicament release). Time-release capsules utilize chemical reactions between chemical substances in the gastrointestinal tract and the coating of the capsules for dissolving and releasing the medicament. Food, particularly proteins and fats, and the GI chemistry affect the speed of the journey of medicaments through the stomach. As such, medicaments, including medicaments available as time-release capsules, do not follow an exact dispensing or dissolving pattern while traveling through the GI tract.

For example, one person may have more than a "normal" amount of chemical substances in the gastrointestinal tract due to a condition, an earlier-administered medicament, etc. and therefore, cause the coating of the time-release capsule to react quicker than normal. Accordingly, the medicament is released by the time-release capsule at a faster rate than an intended rate. However, another person may have less than the "normal" amount of chemical substance in the gastrointestinal tract and cause the coating of the time-release capsule to react slower than normal, thereby releasing the medicament at a slower rate than the intended rate.

Further, as with traditional medicaments available in non-time-release form, time-release capsules require a person or caregiver maintain a log or remember which medicaments to take or administer at different times during the day. For example, some medicaments must be taken at bedtime, such as NSAIDS for rheumatoid arthritis, to produce fewer gastrointestinal complications, such as indigestion. Other medicaments, such as the anti-inflammatory corticosteroid medication prednisone, can cause insomnia when taken in high doses, and are typically taken in the morning. Still, other medicaments, such as antihistamines, are typically taken in the evening to prepare for symptoms that often occur in the morning.

Various ingestible capsules or devices have been disclosed for dispensing medication or taking data readings within the gastrointestinal (GI) tract such as disclosed in US Patent Application Numbers 2005/0158246 published Jul. 21, 2005; 2005/0147559 published Jul. 7, 2005; and 2006/0093663 published May 4, 2006; and U.S. Pat. Nos. 5,318,557 issued on Jun. 7, 1994 and 6,929,636 B1 issued on Aug. 16, 2005.

An additional patent application disclosing an ingestible capsule, the contents of which is hereby incorporated in its entirety by reference is International Publication Number WO 2006/025013 A1 published Mar. 9, 2006, entitled "Electronically Controlled Pill And System For Delivering At Least One Medicament", listing inventor, K. Trovato, (claiming priority from U.S. patent application Ser. No. 60/606,276 filed Sep. 1, 2004 and previously incorporated herein by reference).

However, problems still persist with these systems and methods, especially for treating GI tract diseases such as Inflammatory Bowel Disease (IBD), which includes Crohn's Disease and Ulcerative Colitis, which the herein disclosed methodology and systems overcome.

The present disclosure is directed to an ingestible capsule for dispensing a medicament or like substance in a body, and more particularly in the gastrointestinal tract thereof, the gastrointestinal tract having tissue sites of interest. The capsule, in an illustrative aspect of the present disclosure, preferably includes a medicament reservoir, medicament dispensing means including a plurality of piezoelectric droplet jet nozzle dispensers, a power source (e.g., one or more batteries), electronic control circuitry means communicating with the medicament dispensing means for regulating the amount and time interval for dispensing of the medicament into the gastrointestinal tract by the medicament dispensing means, and an outer protective shell housing the medicament reservoir, the power source, the medicament dispensing means and/or the electronic control circuitry means. Preferably a plurality of the nozzle dispensers of the medicament dispensing means is positioned tangentially to the surface of the housing such that during discharge of the medicament, the capsule is caused to rotate and/or translate so as to discharge the medicament homogeneously onto the tissue sites of interest. In addition, using multiple nozzles and releasing medicament at high speed preferably facilitates medicament absorption by the intestines in the gastrointestinal tract.

Specifically, it is a beneficial aspect of the present disclosure to provide an ingestible capsule for dispensing a medicament in the gastrointestinal tract of a mammal. The gastrointestinal tract having tissue sites of interest. The capsule, accordingly to an illustrative aspect of the present disclosure, preferably has a medicament reservoir for storing the medicament, and medicament dispensing means for dispensing or stopping the dispensing of the medicament from the medicament reservoir into the gastrointestinal tract. The medicament dispensing means in turn preferably has a plurality of piezoelectric droplet jet nozzle dispensers with electronic control circuitry means preferably communicating therewith for regulating the amount and time interval for dispensing of the medicament into the gastrointestinal tract by the medicament dispensing means. The electronic control circuitry means preferably has means for storing or updating of data specific to a pre-determined medicament release profile for the mammal a power source for providing power to the electronic components of the capsule and a non-digestible outer protective shell housing the medicament reservoir, the power source, the medicament dispensing means and the electronic control circuitry means.

Another aspect of the present disclosure is to provide a capsule having sensor means within the capsule for sensing one or more biological conditions in the gastrointestinal tract. The sensor means communicates with the electronic control circuitry means for activating the control circuitry means to dispense medicament according to the medicament release profile, or to determine or modify the medicament release profile. Additionally, or alternatively, the sensor means may include a pressure sensor suitable to detect contraction pressure (e.g., the moment when the intestines contract to power the peristaltic) and communicate with the electronic control circuitry means.

Another aspect is to provide a capsule in which a biological condition sensed by a sensor means is selected from the group consisting of pH level, presence or absence of bacteria or enzymes, anatomical location in the gastrointestinal tract and the presence or absence of blood.

Another aspect is to provide a capsule having a wireless communication means for transmitting and/or receiving signals to and from a second communications means located exterior to the body of the mammal. Upon receiving a signal from the second communications means, the wireless communication means communicates with the electronic control circuitry means to activate the control circuitry means to modify or dispense medicament according to the medicament release profile.

Another aspect is to provide a capsule for administering a medicament for the treatment of a disease in the gastrointestinal tract of a mammal in which the disease is selected from the group consisting of inflammatory bowel disease, celiac disease and intestinal cancer.

Another aspect is to provide a capsule for administering a medicament for the treatment of a disease in the gastrointestinal tract of a mammal wherein the disease is Crohn's Disease or Ulcerative Colitis and the medicament is selected from the group consisting of aminosalicylates, corticosteroids, biologics, anti-coagulant medicaments, immunomodulators, probiotics and antibiotics.

Another aspect is to provide a capsule in which a housing is manufactured from at least one material selected from the group consisting of PELLETHANE 2363 polyetherurethane series of materials, ELASTHANE polyetherurethane, PURSIL thermoplastic silicone polyether urethane, and CARBOSIL silicone polycarbonate urethane.

Another aspect is to provide a capsule having rotational sensor means for sensing when the capsule has made one complete rotation about its axis and communicating with the electronic control circuitry means. The control circuitry means preferably transmits a signal to the dispensing means to stop dispensing the medicament.

Another aspect is to provide a capsule in which an electronic control circuitry means has a real-time clock to provide a reference for elapsed traveling time of the capsule within the gastrointestinal tract.

Another aspect is to provide a capsule in which a plurality of the nozzle dispensers of the medicament dispensing means is positioned tangentially to the surface of the housing such that during discharge of the medicament, the capsule is caused to rotate and/or translate so as to discharge the medicament homogeneously onto the tissue sites of interest.

Another aspect is to provide a method for dispensing a medicament in the gastrointestinal tract of a mammal, the gastrointestinal tract having tissue sites of interest, the method including the steps of (i) orally administering to the mammal an ingestible capsule that includes the medicament, and (ii) dispensing the medicament in the gastrointestinal tract according to a predetermined medicament release profile. The medicament preferably being substantially dispensed at the tissue sites of interest, and the capsule preferably includes a medicament reservoir for storing the medicament, medicament dispensing means for dispensing or stopping the dispensing of the medicament from the medicament reservoir into the gastrointestinal tract. The medicament dispensing means having a plurality of piezoelectric droplet jet nozzle dispensers. The capsule also has electronic control circuitry means communicating with the medicament dispensing means for regulating the amount and time interval for dispensing of the medicament into the gastrointestinal tract by the medicament dispensing means. The electronic control circuitry means having means of storing or updating of data specific to a pre-determined medicament release profile for the mammal. The capsule further has a power source for powering the electronic components thereof, and a non-digestible outer protective shell housing the medicament reservoir, the power source, the medicament dispensing means and the electronic control circuitry means.

Another aspect is to provide a method in which a capsule has sensor means within the capsule for sensing one or more biological conditions in the gastrointestinal tract. The sensor means preferably communicates with the electronic control circuitry means for activating the control circuitry means to dispense medicament according to the medicament release profile, or to determine or modify the medicament release profile. Additionally, or alternatively, the sensor means may include a pressure sensor suitable to detect contraction pressure (e.g., the moment when the intestines contract to power the peristaltic) and communicate with the electronic control circuitry means.

Another aspect is to provide a method in which a biological condition sensed by a sensor means is selected from a group consisting of pH level, presence or absence of bacteria or enzymes, anatomical location in the gastrointestinal tract and the presence or absence of blood.

Another aspect is to provide a method in which a wireless communication means for transmitting and/or receiving signals to and from a second communications means located exterior to the body of the mammal. Upon receiving a signal from the second communications means, the wireless communication means communicates with the electronic control circuitry means to activate the control circuitry means to modify or dispense medicament according to the medicament release profile.

Another aspect is to provide a method for administering a medicament for the treatment of a disease in the gastrointestinal tract of a mammal in which a disease is selected from the group consisting of inflammatory bowel disease, celiac disease and intestinal cancer.

Another aspect is to provide a method for administering a medicament for the treatment of a disease in the gastrointestinal tract of a mammal in which the disease is Crohn's Disease or Ulcerative Colitis and the medicament is selected from the group consisting of aminosalicylates, corticosteroids, biologics, anti-coagulant medicaments, immunomodulators, probiotics and antibiotics.

Another aspect is to provide a method in which a housing is manufactured from at least one material selected from the group consisting of PELLETHANE 2363 polyetherurethane series of materials, ELASTHANE polyetherurethane, PURSIL thermoplastic silicone polyether urethane, and CARBOSIL silicone polycarbonate urethane.

Another aspect is to provide a method utilizing rotational sensor means for sensing when the capsule has made one complete rotation about its axis and communicating with the electronic control circuitry means. The control circuitry means transmits a signal to the dispensing means to stop dispensing the medicament.

Another aspect is to provide a method in which an electronic control circuitry means has a real-time clock to provide a reference for elapsed traveling time of the capsule within the gastrointestinal tract.

Another aspect is to provide a method in which a plurality of the nozzle dispensers of the medicament dispensing means is positioned tangentially to the surface of the housing such that during discharge of the medicament, the capsule is caused to rotate and/or translate so as to discharge the medicament homogeneously onto the tissue sites of interest.

These and other aspects of the present disclosure are explained in more detail with reference to the following exemplary embodiments and with reference to the figures.

FIG. 1A is a schematic diagram of an electronically controlled capsule taken, in large part, from International Publication Number WO 2006/025013 A1 published Mar. 9, 2006, entitled "Electronically Controlled Pill And System For Delivering At Least One Medicament", listing inventor, K. Trovato, (claiming priority from U.S. patent application Ser. No. 60/606,276 filed Sep. 1, 2004).

Figure 3:
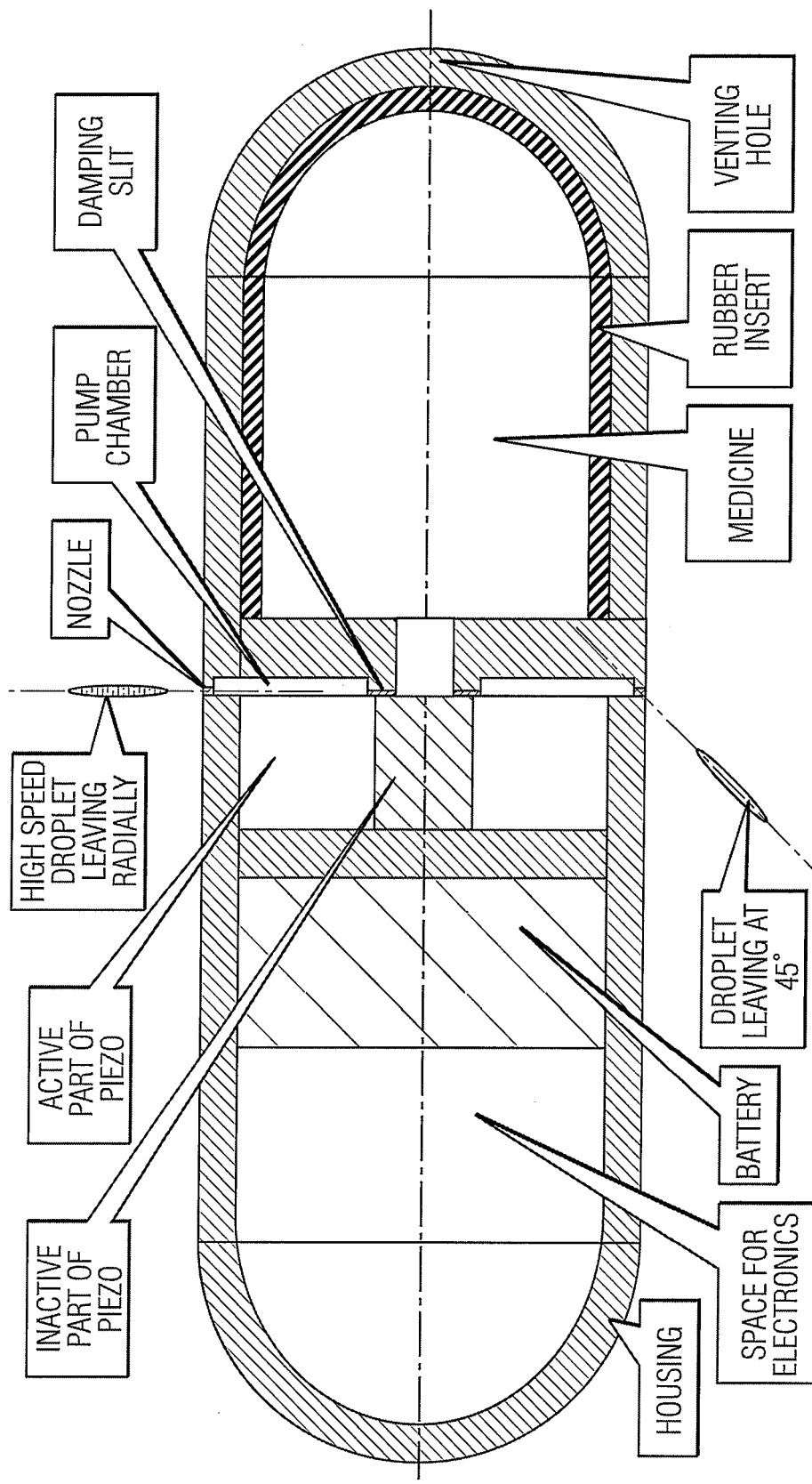

FIG. 3 conceptually depicts an aspect of an ingestible capsule for dispensing medicament according to an aspect of the present disclosure.

Figure 4:
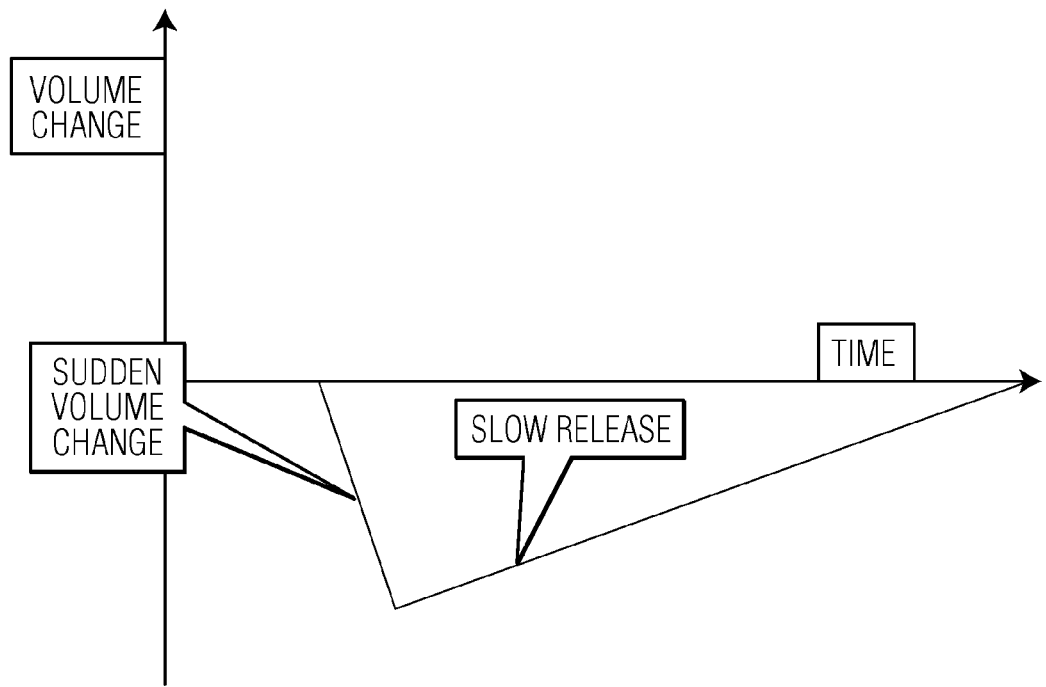

FIG. 4 is a chart illustrating a typical pattern of volume change with time in the pumping chamber of a jet nozzle dispenser according to an aspect of the present disclosure.

Figure 5:
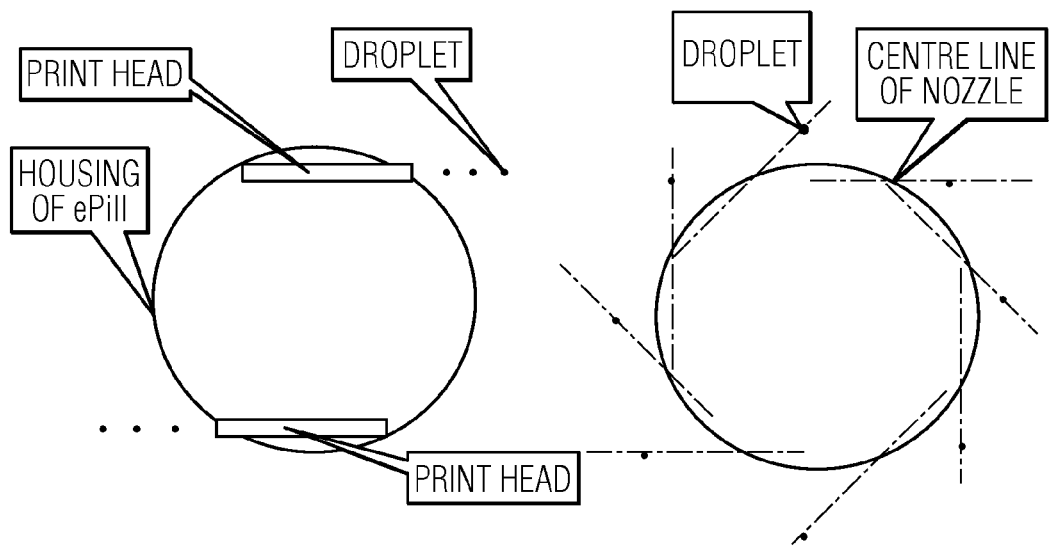

FIG. 5 is a conceptual representation of an ingestible capsule having multiple print heads with the jet nozzles positioned so that the medicament jet discharges tangentially to the circumference of the capsule housing surface, causing the capsule to rotate according to an aspect of the present disclosure.

According to the disclosure in International Publication Number WO 2006/025013 A1 published Mar. 9, 2006, entitled "Electronically Controlled Pill And System For Delivering At Least One Medicament", listing inventor, K. Trovato, (claiming priority from U.S. patent application Ser. No. 60/606,276 filed Sep. 1, 2004), which is incorporated in its entirety by reference herein, an electronically controlled capsule or medicament delivery system is disclosed for delivering or dispensing a medicament according to a preset dispensing timing pattern while traversing through the gastrointestinal tract. The preset dispensing timing pattern is fixed and is not susceptible to a person's physiological processes and conditions, mood, earlier-administered medicaments, etc. The electronically controlled capsule includes control and timing circuitry for controlling the opening and closing of a valve or hatch according to the preset dispensing timing pattern for dispensing a medicament stored within a medicament reservoir of the capsule. The electronically controlled capsule allows a person to take all capsules substantially simultaneously, at say 7:00 am, so that no more capsules are required for the day. Medication that does not fit into one electronically controlled capsule can be coordinated with other electronically controlled capsules for the full day's pay load regimen.

Figure 1A:
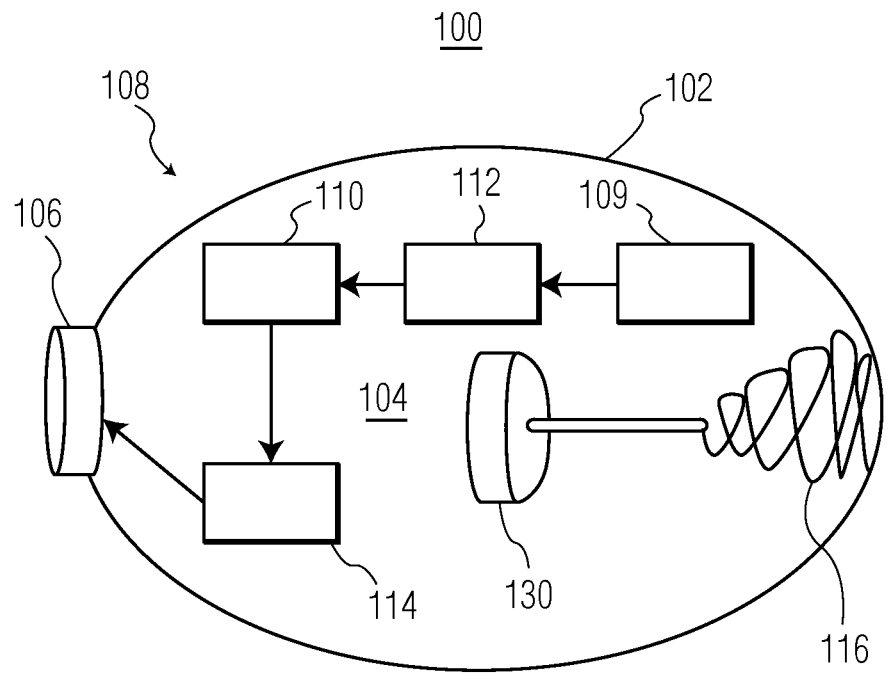
FIG. 1B is a conceptual representation from FIG. 1A of an ingestible electronically controlled capsule or capsule for dispensing medicament according to an aspect of the present disclosure.

As is shown in FIG. 1A the electronically controlled capsule 100 includes programmed electronics that control a release mechanism according to a dispensing pattern for dispensing a medicament. The capsule 100 is made from bio-compatible materials such that the capsule 100 is bio-compatible for at least the amount of time it requires to traverse the gastrointestinal tract. The bio-compatible materials are preferably stable at room temperature, such that the capsule has a long shelf life. As used herein and in the claims the word "medicament" refers to medicines, non-medicinal substances, contrast agents, gases, fluids, liquids, chemicals, radiological agents, imaging markers, sensors for monitoring the person's vitals, etc. As illustratively depicted, the electronically controlled capsule 100 may include an outer shell or housing 102; a medicament reservoir 104 for storing a medicament; an electronically controlled release valve or hatch 106 for dispensing the medicaments stored in the medicament reservoir 104; control and timing circuitry 108 for opening and closing the valve 106; and a power source 109, for example, one or more batteries. The control and timing circuitry 108 opens and closes the valve 106 throughout a dispensing time period in accordance with a preset dispensing timing pattern. The control and timing circuitry 108 includes timing circuitry 110 programmed with the preset dispensing timing pattern, a start timer mechanism 112 which includes a real-time clock to provide a reference for elapsed traveling time of the capsule in the GI tract, a release controller 114 and a pressure mechanism 116 for applying pressure to a piston-type member 130 for forcing the medicament within the reservoir 104 towards the valve 106. The start timer mechanism 112 enables activation of the timing circuitry 110. The power source 109 powers the electronic components of the capsule, for example, the control and timing circuitry 108, sensor means 132, rotational sensor means 134, etc., in order for each of the electromechanical components to operate during the dispensing time period.

The shell 102 is preferably manufactured from materials used to fabricate implantable devices, including pacemaker leads and cardiac prosthesis devices, such as artificial hearts, heart valves, intraaortic balloons, and ventricular assist devices. These materials include PELLETHANE 2363 polyetherurethane series of materials available from Dow Chemical Company and Elasthane polyetherurethane available from the Polymer Technology Group, Inc. Other materials include PURSIL thermoplastic silicone polyether urethane, and CARBOSIL silicone polycarbonate urethane, also available from the Polymer Technology Group, Inc.

According to another aspect of the present disclosure, an ingestible capsule for dispensing a medicament in the gastrointestinal tract of a mammal is disclosed having medicament dispensing means including a plurality of piezoelectric droplet jet nozzle dispensers. The nozzle dispensers of the medicament dispensing means are positioned tangentially to the surface of the housing such that during discharge of the medicament, the capsule is caused to rotate so as to discharge the medicament homogeneously onto the tissue sites of interest in the GI tract. More particularly, the present disclosure relates to an ingestible capsule for dosing medicaments or medicaments in a controlled way, as far as place and amount are concerned, in the gastrointestinal tract.

The capsule, in an exemplary aspect of the present disclosure, is swallowable, about 1 cm in diameter and 2 to 3 cm's long, and contains, for example, one or more batteries for powering the electronic control circuitry, sensors and any other electronics in the capsule, a medicine reservoir containing medicine, electronics for controlling the medicine release, and one or more multi nozzle miniature ink jet printing heads. By activating the print heads the medicine is released. The print heads are placed such that they eject the medicine in a direction tangential to the circumference of the capsule surface. When ejecting the medicine the capsule rotates and/or translates, thereby spreading the medicine homogeneously over the interior of the intestine. In addition, by using multiple nozzles and releasing medicament at high speed, this facilitates medicament absorption by the intestines in the gastrointestinal tract.

Still further, according to another aspect of the present disclosure, the medicament accommodated by the capsule may be retained in one or more micelles, such as, for example, polymeric micelles. As will be readily appreciated by those skilled in the art, a micelle is a colloidal aggregate of amphipathic molecules for which the polar hydrophilic portions of the molecule extend outwardly while the non-polar hydrophobic portions extend inwardly. Polyoxyethylene ethers, alkali metal alkyl sulfates and bile acids are a few exemplary micelle-forming compounds. See, [Cammas-Marion, S., T. Okano, and K. Kataoka. Functional and site specific macromolecular micelles as high potential medicament carriers. Colloids and Surfaces B: Biointerfaces 1999; 16: 207-215.], and [Lavasanifar, A., J. Sammuel, and G. S. Kwon. Poly(ethylene oxide)-block-poly(Lamino acid) micelles for medicament delivery. Advanced Medicament Delivery 2002; 54: 169-190.], for a more detailed discussion of how micelles may serve as a medicament delivery vehicle by either physically entrapping medicament in the core thereof (i.e. hydrophobic medicaments can be trapped inside the micelle by hydrophobic interactions), or by chemically conjugating a medicament to the hydrophobic block prior to micelle formation.

Figure 1B:
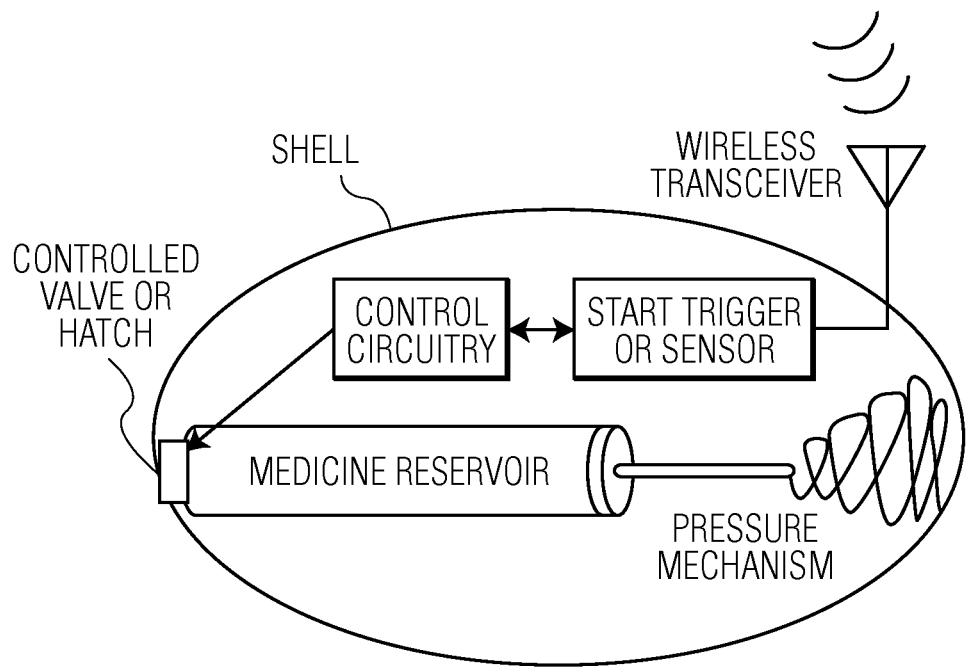

An initial concept diagram of an electronically controlled dosing capsule according to an aspect of the present disclosure is shown in FIG. 1B, which is based on the disclosure in the aforementioned publication WO 2006/025013. The capsule has a shell containing control electronics for precisely delivering medication and a link for wireless communication to outside the body. The addition of electronics and/or communication creates the ability to deliver medication:

a) at the site, using sensors, timing, or location
    b) in a more concentrated amount
    c) with a catalyst or in combination with another medicament
    d) precisely controlled for smooth or patterned delivery
    e) more intensely by using a stent-style balloon to temporarily stop/slow progress of the capsule along the gastrointestinal (GI) tract.
    f) via radio control from outside the body in order to:
        i) adjust the medication en-route
        ii) stop the delivery in case of adverse reaction
        iii) customize the medication delivery rate and pattern to an individual patient, for instance to compensate for surgical locations, length of GI, kidney function, liver toxicity, etc.
        iv) trigger release at a particular time (example: 2 hours prior to waking-up)
        v) release in response to externally collected/reported data (e.g. # nighttime wakings, pollen count, etc.).

When considering the design of an electronic swallowable capsule, it is desirable to have dispensing means for the medicament while traversing the GI tract of a mammal (e.g. human being) which provides a dosing or dispensing mechanism or medicament release profile that is fully electronically controllable. This is achieved in accordance with an aspect of the present disclosure, e.g., utilizing the capsule and methodology incorporating dispensing means having piezoelectric droplet jet nozzle dispensers which are based on piezoelectric inkjet printer technology. With an inkjet printer head, a single medicament droplet has a very small volume (about 3 nl) and in one second up to 1000 droplet can be dispensed by one nozzle. This means that the release rate can have a dynamic range of factor 1000. Currently, for an orally administered medicine, medicament release rate is controlled by chemical formulation, which has to be developed and adjusted case by case (one for each medicament). The actual release rate of a given formulation can vary from patient to patient depending on individual GI tract conditions. Thus, there is no universal method to control release rate of orally taken medicaments. Moreover, there are no known means and methods for enhancing absorption of medicines by the intestines, for example, by penetrating through the mucous layer as is disclosed herein according to the present disclosure.

The capsule and methodology according to a preferred aspect of the present disclosure utilizes an inkjet printer pump (based on piezoelectric component) to dispense medicament according to a programmable profile. Since the minimum dose is determined by the volume of each droplet, which is very small and independent of medicament reservoir level, a well defined medicament release profile can be achieved. In addition, the medicament can be distributed more evenly in space than could be achieved heretofore by using multiple nozzles and releasing medicament at high speed to facilitate medicament absorption by the intestines. Among the benefits of delivering the medicament according to a specific release profile, these include much improved flexibility and control over the time, place and amount of medicament dispensed according to a medicament release profile in the GI tract, and the ability to maintain desired bioavailability (a constant or variable concentration) of medicament in the body for optimum therapy efficacy.

The bio-compatible materials are preferably stable in room temperature, such that the capsule has a long shelf life. Although the disclosure and examples refer to the capsule being utilized in the dispensing of medicaments or medicaments, it is understood that other substances can be dispensed such as non-medicinal substances, contrast agents, gases, fluids, liquids, chemicals, radiological agents, imaging markers, sensors for monitoring the person's vitals, etc.

Some examples of GI tract diseases that can be treated using the capsule and methodology disclosed herein are inflammatory bowel disease (IBD), celiac disease and intestinal cancer. Some examples of medicaments that can be used in treating IBD, particularly Crohn's Disease or Ulcerative Colitis are aminosalicylates, corticosteroids, biologics, anticoagulant medicaments, immunomodulators, probiotics and antibiotics.

One of the major advantages of the exemplary capsule and methodology disclosed herein is control over the medicament delivery profile. The range of profiles envisioned range from a quick burst, to an arbitrary function spread over a time of a natural body passage that can be up to 48 hours. In an aspect of the present disclosure, the capsule has on-board sensors to detect sites of disease or locations where the medication is best applied, as well as other factors/conditions facilitating optimal medication application.

For example, a capsule according to an aspect of the present disclosure, during its travel through the intestines, drifts from the pylorus to the ileocecal valve at or about 1 m/hour or so. Due to the peristaltics of the small intestines, e.g., superposed on the drift velocity, large velocity variations are often present pushing the capsule back and forth as it passes along the intestines. This means that medication released from the capsule is often thoroughly mixed before it becomes effective, which may or may not be beneficial. That is, in the intestines strong mixing takes place, medication is typically dissolved in quite a large volume resulting in the effective concentration being often low at the spots where it is intended/needed. Hence, for most medication applications, the most effective interval in time for releasing the medication is during contraction of the intestines, as it is during contraction that the intestines tightly close around the capsule such that medication may be dispensed so as to come into direct contact with the surface walls of the intestines. For instance, medication may be placed directly onto the mucus layer on surface structures (e.g., villi). Further, using high speed jetting systems, such as discussed herein, suitable for dosing, medication can be directed into and/or through the mucus layer and eventually directly into the blood circulation system.

In an aspect of the present disclosure, a pressure transducer may be operatively associated with a capsule to detect the moment of contraction around the capsule so as to beneficially enable delivery of medication and/or the like at the moment the intestines contract, and thereby bring the medication or the like immediately in contact with the walls of the intestines. For example, when a suitable capsule is positioned at a target location and a pressure transducer or the like detects a contraction of the intestine, medication(s) and/or treatment(s) may be released/delivered and/or performed.

In another aspect of the present disclosure, medication or like substance may be incorporated into a dissolvable ointment chosen so that preferably it adheres to intestinal tissue more readily than a capsule carrying the ointment. For example, a capsule may be provided with a surface having at least limited adhering characteristics (e.g., Teflon), and the ointment dispensed or released from the capsule via one or more apertures therein.

In still another aspect of the present disclosure, medication or the like may be associated with a low viscous fluid (e.g., dissolved) so as to be dispensable via, e.g., a piezo driven high speed droplet dispenser such as, e.g., discussed/disclosed herein. Such a piezo device is preferably capable of delivering medication through at least a mucus layer, and by increasing dispensing velocity further, medication or the like may be delivered so as to penetrate through intestinal epithelial tissue where it is directly taken into blood circulation.

In yet another aspect of the present disclosure, medicament dispensing means of a capsule may have at least the following features/elements: (i) the dosing mechanism is based on the use of piezo ink jet technology; (ii) piezo ink jet technology only generates pressure in order to eject droplets for depositing the medicament or medicine on the inside of the intestines, so the medicine to be applied will not be harmed; (iii) multi nozzle miniature print heads are used to increase the reliability of the medicine dosing; (iv) dosing is done at a high speed, say up to 50 meters/second (m/s) in order to be sure that the medicine reaches the wall of the intestines despite the fact that the nozzles may be covered with faeces; this is based on studies involving teeth cleaning where it was found that gum can withstand safely droplet velocities up to 50 m/s); (v) the nozzles eject medicament tangentially such that during jetting the capsule rotates and/or translates and the inside of the intestines are covered with medicine homogeneously.

According to another aspect of the present disclosure, in designing the dispensing means and capsule, we consider, for example a capsule or pill of length 26 mm and radius 5.5 mm, the capsule is closed with two spherical caps of radius 5.5 mm. The dimensions refer to the outside. A wall of about 1 mm thickness of thermoplastic material will suffice to enclose the interior of the capsule hermetically.

The total inside volume enclosed equals:

$$v = \frac{4}{3}\pi R_{pill}^3 + \pi R_{pill}^2 L_{pill}$$
$$= \frac{4}{3}\pi(4.5)^3 + \pi(4.5)^2 15$$
$$= 1336 \text{ mm}^3.$$

To start with, let us assume that about ⅓ is payload (i.e., medicament substance).

This means that the payload measures 500 mm³ (0.5 ml or 500 µl).

The space for the battery is, for example, 100 mm³. The energy content of, for example, a zinc/alkaline electrolyte battery is 575 Wh/l. The energy content of the battery used in the capsule defined above is 57.5 mWh=207 J. A silver-oxide battery of similar dimensions has about one half the energy content, and an alkaline battery has about one quarter the energy content.

Basically, a typical ink jet printer head is a valveless pump device that displaces dropletwise fluid from a reservoir to the outside of the capsule. The payload can be dispensed in 1.66*10⁵ droplets of 3 nl volume. According to an aspect of the present disclosure, the design is based on high-speed droplets. These droplets leave the print head as long slender jets rather than as a series of well-defined droplets. A jet of volume, $V_{jet}$=3 nl, needs a hole of about 100 µm diameter ($R_{jet}$=50 μm) and has a length $L_{jet}$=382 μm. When deposited on the inside of the intestines such a short jet is supposed to spread to a dot with say 500 μm diameter. The mean film thickness of such a dot is 15 μm. With $1.66*10^5$ of such dots an area of 3 dm² can be covered.

The short jet leaves the capsule and nozzle with a speed of 25 m/s. At this speed the jet frees the nozzle from debris out of the faeces and has the power to penetrate slightly through the mucus layer on the inside of the intestines. The total energy of the droplet is the surface energy and the kinetic energy:

$$E = \sigma\{4*\pi R_{jet}^2 + 2*\pi*R_{jet}*(L_{jet}-2R_{jet})\} + \frac{1}{2}\rho V_{jet}v^2$$

$$= 0.03*\begin{Bmatrix} 4\pi*(50*10^{-6})^2 + \\ 2*\pi*50* \\ 282*10^{-12} \end{Bmatrix} + \frac{1}{2}1000*3000*10^{-15}25^2$$

$$= 3.6*10^{-9} + 9.375*10^{-7}$$

$$= 9.41*10^{-7} \text{ J.}$$

The surface tension has been set equal to 0.03 N/m and the density to 1000 kg/m³. Note that the contribution of the surface tension is very small and can be neglected.

For $1.66*10^5$ droplets the droplet energy equals 157 mJ: considerably less than the energy content of the battery.

For a droplet leaving the system with 50 m/s the kinetic energy per droplet is four times higher and the total energy needed is still less than 1 J.

Figure 2:
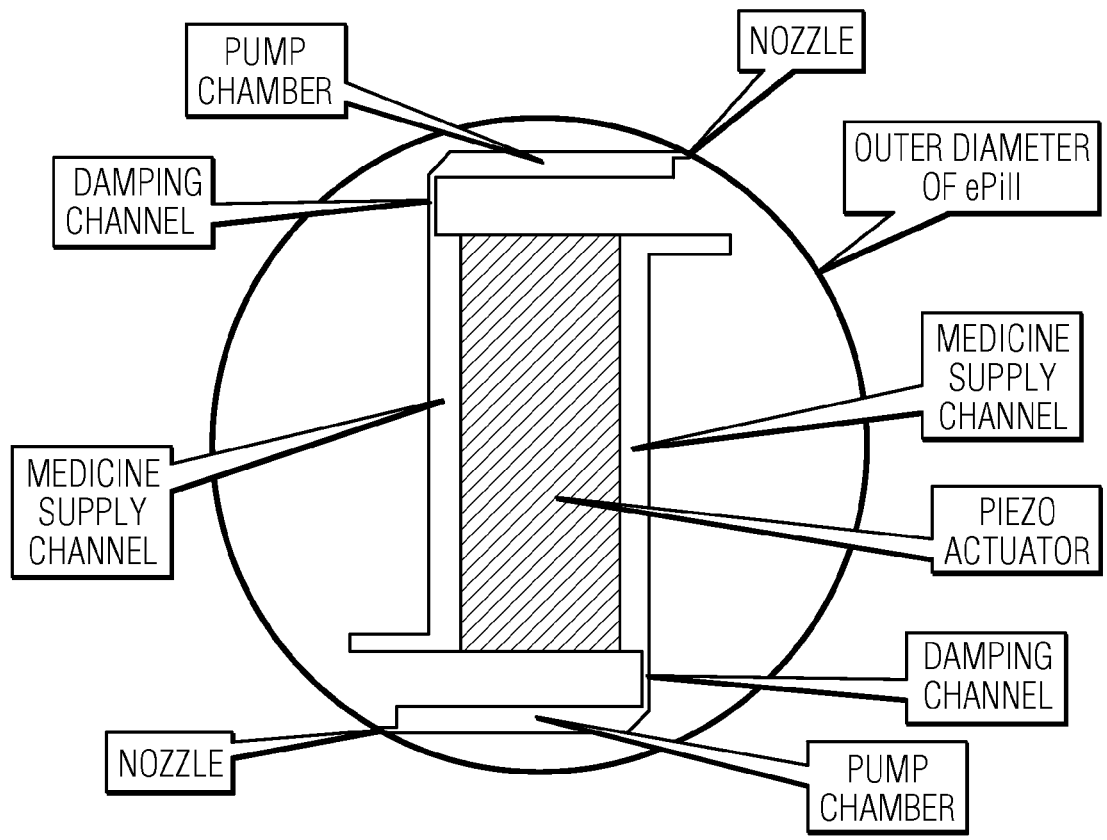
FIG. 2 is a conceptual representation of the basic design of an inkjet printer pump according to another aspect of the present disclosure.

A basic design of an inkjet printer pump according to an aspect of the present disclosure is shown in the FIG. 2. The pump section of the capsule (referred to as capsule) is made of a stainless steel housing with outside diameter of 11 mm in which by wire spark erosion a channel lay-out is machined. The layout consists of two pump chambers with length of 4 mm and a width of 13.5 mm. The height of the pump chambers equals 0.32 mm. The pump chambers are connected to the outside of the capsule by a series of 5 nozzles with inside diameter of 100 μm and length 100 μm, drilled, or made otherwise, at a pitch of 3 mm. To the inside they are connected by slits of 1 mm long, 13.5 mm wide and 0.1 mm high. A block of piezo active material, placed between the two pump chambers, actuates the pumps. Upon actuating the piezo, it extends and closes the height of the pump chambers generating pressure needed to accelerate the fluid inside the nozzles. Next to the piezo there is room for conveying the medicine to the pump chambers.

FIG. 3 shows an aspect of the capsule according to the present disclosure. Here the nozzles are placed in one cross-section. One disc-shaped piezo drives the nozzles. In this set-up it is supposed to have 10 nozzles along the circumference of the capsule. The jets leave the system almost tangentially as shown in FIG. 5. The print head structure being the damping slit, the pump chamber and the nozzles are machine by MEMS technology. All the nozzles are driven at the same time by one single piezo. Also shown are a venting hole and a rubber bag. The medicine is put in the rubber bag; the venting hole takes care of keeping the pressure inside the medicine equal to the pressure at the nozzle. In that way no spontaneous leakage occurs due to pressure variations inside the gastrointestinal tract.

The calculation of the basic dimensions of the high-speed droplet generator follows the way of thinking of J. F. Dijksman, "Hydroacoustics of piezoelectrically driven print heads", Flow, Turbulence and Combustion, Volume 1, No. 1 (1999), pp. 1-30. We consider here a set-up of a nozzle with radius $R_1$ ($A_1=\pi R_1^2$) and length $L_1$ connected to a pump chamber with volume V. The pump chamber is connected to the fluid supply by a small damping channel with cross section $A_2$ and length $L_2$. The volume of the pump chamber is suddenly changed by an amount ΔV. ΔV is considered positive if the volume of the pump chamber is diminished. For the action of this type of pump it is essential that the pump is driven by a sudden volume change rather than by a pulse wise volume change as is usual in standard print heads. A typical volume change time curve is shown in FIG. 4.

Without going into the details how the jet breaks up into droplets we assume that the volume change is transferred into the volume of the jet and into the droplet or droplets. We list here the relevant formulas from the paper mentioned above:

$$p(t) = \rho c^2 \frac{\Delta V}{V}\cos\omega_H t = \Delta p \cos\omega_H t,$$

$$v_1(t) = \frac{\Delta p}{\rho\omega_H L_1}\sin\omega_H t,$$

$$\omega_H = c\sqrt{\frac{1}{V}\left(\frac{A_1}{L_1} + \frac{A_2}{L_2}\right)},$$

$$V_{droplet} \approx \Delta V,$$

where c is the speed of sound of the fluid corrected for the compliance of the pump chamber, $\omega_H$ the Helmholtz frequency and $v_1$ the velocity of the fluid column in the nozzle.

The design strategy is as follows. We aim for a high droplet speed, at a given droplet/jet volume.

Rewriting the formula for the velocity of the fluid in the nozzle we have:

$$v_1 = \frac{\omega_H \Delta V}{\left(\frac{A_1}{L_1} + \frac{A_2}{L_2}\right)L_1}\sin\omega_H t,$$

$$v_{1,max} = \frac{\omega_H \Delta V}{\left(\frac{A_1}{L_1} + \frac{A_2}{L_2}\right)L_1} \approx \frac{\omega_H \Delta V}{A_1},$$

$$\omega_H = \frac{v_{1,max}\left(\frac{A_1}{L_1} + \frac{A_2}{L_2}\right)L_1}{\Delta V} = \frac{v_{1,max}A_1}{\Delta V}.$$

The compressibility of the fluid, the pressure amplitude and the relative volume change are given by:

$$\Delta p = K\frac{\Delta V}{V}$$

$$K = \rho c^2$$

The velocity of sound must be corrected for the compliance of the walls of the pump chamber. Usually the value of 1000 m/s is used for initial calculations.

All calculations can be carried out for one nozzle, so the width of the pump chamber equals the pitch of the nozzles, namely 3 mm.

For a maximum velocity of 25 m/s and the geometrical data listed above the Helmholtz frequency appears to be 50 kHz and Δp 7.85 bar.

The relative volume displacement equals $7.85*10^{-4}$. The inside volume of the pump is 3.82 mm$^3$. The energy stored in the pressurized fluid flows from:

$$E_{pressure} = \frac{1}{2}\Delta p \Delta V$$
$$= \frac{1}{2}KV\left(\frac{\Delta V}{V}\right)^2$$
$$= 0.5*1000*1000^2*3.82*10^{-9}*(7.85*10^{-4})^2$$
$$= 1.18*10^{-6} \text{ J}.$$

This amount of energy cannot be retrieved and must be considered as lost. Per $1.66*10^5$ short jets this is still far within the energy budget of the battery.

The droplets are generated by charging the piezo actuator. The energy stored in the actuator follows from:

$$E_{actuator} = \frac{1}{2}cu^2,$$
$$c = \frac{\text{Area} * E_{modulus}}{\text{thickness}}$$
$$= \frac{0.003 * 0.0135 * 8.8 * 10^{10}}{7 * 10^{-3}}$$
$$= 5.09 * 10^8 \text{ N/m},$$
$$E_{actuator} = 0.5 * 5.09 * 10^8 * (2 * 7.854 * 10^{-4} * 0.32 * 10^{-3})^2$$
$$= 6.43 * 10^{-5} \text{ J}.$$

The pump must preferably be charged stepwise. If no care is taken to re-use the energy stored in the piezo the energy calculated above is lost. As the actuator drives 10 nozzles for $1.66*10^5$ droplets this is 1.07 J. It depends on the quality of the design how much energy is lost in the electronics. As the piezo is long it can be driven at relatively low voltages (up to say a few volts when using multiplayer piezo's). The circuitry in the capsule has to upgrade the low battery voltage to the voltage for driving the piezo's. This will cause extra losses in the system.

The multi nozzle print heads may, e.g., be mounted as depicted in FIG. 5.

Initially the droplet leaves the nozzle as a high-speed jet. The exit pressure of a jet issuing from a nozzle can be calculated as follows. Consider the pump as a closed system from which a small jet with velocity v and cross section A is flowing into space. The force exerted by the leaving jet on the system equals:

$$F = ma = \frac{d}{dt}mv = v\frac{d}{dt}m = v\rho A_{nozzle}v = \rho A_{nozzle}v^2,$$

This force has to balanced by a pressure inside the nozzle, $$p = \frac{F}{A_{nozzle}} = \rho v^2$$

For a jet leaving the nozzle with a speed of 25 m/s this pressure equals 6.25 bar. It should be noted that this pressure has not to be generated in he pump chamber, as the cross-sectional area of the nozzle is much smaller than the cross-sectional area of the pump chamber.

The following approximate calculation shows the effect of the tangential jetting print heads on the rotational positioning of the capsule inside the intestines.

It is tacitly assumed that most of the mass is in the housing of the capsule.

$$F = m\ddot{x}$$
$$FR = M = Cm\frac{\ddot{x}}{R}R^2 = CmR^2\ddot{\varphi}$$

Here m denotes the mass of the capsule and x the tangential displacement at the nozzle induced by the leaving high velocity jet. C is a coefficient that takes into account that not all the mass is located in the cylindrical housing of the capsule (C is between ¼ and 1). R is the outside radius of the device. F is a force and M a moment.

The capsule is surrounded by the contents of the intestines or by the wall of the intestine itself. At the very moment the capsule starts to rotate it experiences viscous drag opposing the rotational motion. The viscous drag can be estimated by:

$$\dot{x} = R\dot{\varphi}$$
$$\dot{\gamma} = \frac{\dot{x}}{h_{film}} = \frac{R\dot{\varphi}}{h_{film}}$$
$$\tau = \eta\dot{\gamma}$$
$$M_{viscous\ drag} = \tau A_{pill}R = \eta\frac{R\dot{\varphi}}{h_{film}}2\pi RLR$$

With η the viscosity of the mucus layer of the inside of the intestines, of the fluid like substance contained in the small intestine of the more solid like content of the colon. The thickness of the fluid layer between capsule and the wall of the intestine is denoted by $h_{film}$. The force exerted by the leaving jet lasts only for a short time. As a jet has to leave rather than the formation of a droplet for our calculations we take the period time of the basic frequency $f_{Helmholtz}$ (Helmholtz frequency, say 50 kHz).

The moment forcing the capsule to rotate is given by:

$$M_{jetting} = N\rho A_{nozzle}v^2 R\frac{f}{f_{Helmholtz}}$$

N is the number of nozzles used for jetting the medical fluid and f the driving frequency of the print heads installed.

The equation of motion of the capsule reads:

$$CmR^2\ddot{\varphi} + \eta\frac{2\pi R^3 L}{h_{film}}\dot{\varphi} = N\rho A_{nozzle}v^2 R\frac{f}{f_{Helmholtz}}$$

The solution of this first order linear differential equation is governed by a time constant and the ultimate rotational speed.

$$\tau = \frac{C}{2\pi}\frac{mh_{film}}{\eta RL}$$

-continued $$\varphi = \frac{N}{2\pi} \frac{\rho}{\eta} \frac{A_{nozzle} v^2 h_{film}}{R^2 L} \frac{f}{f_{Helmholtz}}$$

As an example, the following values were used:
m=0.002 kg, C=⅓, $h_{film}$=10 μm, η=0.001 Pas (water), R=5.5 mm, L=26 mm, ρ=1000 kg/m³, $A_{nozzle}$=7.85*10⁻⁹ m², v=25 m/s, f=1000 Hz, $f_{Helmholtz}$=50 kHz and N=10.

The time constant T=7.42 msec and the ultimate rotational speed is 2.0 rad/sec. These numbers tell us that almost immediately the capsule reaches its ultimate speed and that for one turn it takes about 3 seconds. Per 3 seconds 3*1000*10 droplets are formed being ⅕ of the total payload. So the procedure described here one rotation per medicine application can be repeated 5 times. The nozzles are mounted at a pitch of 3 mm. The two heads are mounted such that the nozzles are interlaced at a distance of 1.5 mm. So per rotation about 1.5 cm can be covered with medication and per payload roughly 5 to 7.5 cm of the inside of the intestines. Of course the concentration will determine how many turns are needed to arrive at the doses per unit area prescribed.

Up to now it has been assumed that the nozzles are directed tangentially outwards. They can be drilled under an angle such that the leaving fluid jets not only let the capsule rotate but also propel the capsule forward. Suppose the jets are placed under 45°. The force generated by the leaving jets equals:

$$F_{jetting} = N\rho A_{nozzle}v^2\frac{f}{f_{Helmholtz}}\frac{1}{2}\sqrt{2}$$

The viscous drag force:

$$F_{viscous\ drag} = \eta\frac{\dot{x}}{h_{film}}2\pi RL$$

here the time derivative refers to the axial displacement of the capsule. After a short start-up phenomenon (nor calculated here anymore) the velocity of the capsule is calculated:

$$\dot{x} = \frac{N\rho A_{nozzle}v^2 h_{film}}{2\pi\eta RL}\frac{f}{f_{Helmholtz}}\frac{1}{2}\sqrt{2}$$

Using the same data as before the axial velocity appears to be 7.7 mm/s. So during 3-4 seconds (the rotation becomes slower) of spitting droplets it moves 23 up 30 mm. In this way a larger area of the intestines is covered during medicine application.

It should be noted that the analysis is only approximate and a large number of phenomena are not included such as: (i) the viscosity may be considerably larger slowing down the rotation, (ii) only a part of the capsule is in close connection to the wall lowering the viscous drag resulting is a much higher rotational and axial speed, (iii) some nozzles may be clogged lowering the driving force and lowering the rotational and axial speed, (iv) the peristaltic of the intestines also helps the capsule to move forward.

In still another illustrative aspect of the present disclosure, the capsule incorporates a rotational sensor that detects the rotation of the capsule around its axis. Dosing of medicine stops, for example, at the moment a defined rotational amount is reached (e.g., a complete revolution is made).

In yet still another illustrative aspect of the present disclosure, the medicament is retained by micelles. It is believed that the use of micelles may significantly aid in the absorption of a medicament or medicament formulation both because of the micelles' enhanced absorption ability, and because of their size and/or shape. That is, according to an aspect of the present disclosure, one or more micelles sized, for example, in the range of about 1 to 10 nanometers, and having any of a variety of shapes (e.g., prolate, oblate, spherical, etc.) preferably encapsulate and/or protect medicament molecules from degradation. The formulation may be provided as a jet spray via, for example, the capsule and/or dispensing means discussed herein so as to provide a relatively high velocity fine droplet output to one or more tissue sites of interest. It will be appreciated by those skilled in the pertinent art that the effective formulation amount will vary depending on the particular medicament and/or micelle used, the parameters determined for the medicament, the nature and/or severity of the treatment, the patient being treated, and the route of administration.

While the present disclosure has been described with respect to specific illustrative aspects thereof, it will be recognized by those of ordinary skill in the art that many modifications, enhancements, and/or changes can be achieved without departing from the spirit and scope of the present disclosure. Therefore, it is manifestly intended that the present disclosure be limited only by the scope of the claims and equivalents thereof.

The invention claimed is:

1. An ingestible capsule for dispensing a medicament at or near tissue sites of interest, the capsule comprising:

a sidewall;

a medicament reservoir for storing the medicament, disposed within the sidewall;

at least one piezoelectric droplet jet nozzle dispenser in fluid communication with the medicament reservoir, each at least one piezoelectric droplet jet nozzle dispenser including a nozzle arranged to eject medicament through the sidewall, along a dispensing axis angled at a non-zero angle relative to an axis normal the sidewall at the nozzle;

a controller communicating with the dispenser to control release of the medicament through the nozzle; and a power source for providing power to one or more components of the capsule.

2. The capsule of claim 1, further comprising a sensor adapted to sense one or more biological conditions; wherein the sensor cooperates with the controller to selectively dispense the medicament according to the medicament release profile, and/or to determine and/or modify such medicament release profile.

3. The capsule of claim 2, wherein the biological condition sensed by the sensor is selected from a group consisting of pH level, presence or absence of bacteria or enzymes, anatomical location at or ncar the tissue site of interest, and the presence or absence of blood.

4. The capsule of claim 1, further comprising a wireless communicator adapted to transmit signals to and/or receive signals from a remote communicator, wherein when the wireless communicator is adapted to receive signals, upon receiving a signal from the remote communicator, the wireless communicator cooperates with the controller so as to modify and/or dispense the medicament according to the medicament release profile.

5. The capsule of claim 1, wherein the capsule is used to administer a medicament intended to treat a disease selected from a group consisting of inflammatory bowel disease, celiac disease and intestinal cancer.

6. The capsule of claim 1, wherein the capsule is used to administer a medicament intended to treat Crohn's Disease or Ulcerative Colitis and the medicament is selected from a group consisting of aminosalicylates, corticosteroids, biologics, anti-coagulant medicaments, immunomodulators, probiotics and antibiotics.

7. The capsule of claim 1, wherein the capsule has a housing that is manufactured from at least one material selected from a group consisting of PELLETHANE 2363 polyetherurethane series of materials, ELASTHANE polyethemrethane, PURSIL thermoplastic silicone polyether urethane, and CARBOSIL silicone polycarbonate urethane.

8. The capsule of claim 1, further comprising a sensor adapted to sense rotation of the capsule.

9. The capsule of claim 1, wherein the controller comprises a real-time clock to provide a reference for elapsed traveling time of the capsule within the gastrointestinal tract.

10. The capsule of claim 1, wherein ejection of medicament along the dispensing axis causes the capsule to rotate, thereby discharging the medicament homogeneously onto the tissue sites of interest.

11. A method for dispensing a medicament in the gastrointestinal tract of a mammal, the gastrointestinal tract having tissue sites of interest, the method comprising:
orally administering an ingestible capsule accommodating the medicament, the capsule comprising a sidewall; a medicament reservoir within the sidewall storing a medicament; and at least one piezoelectric droplet jet nozzle dispenser including a nozzle arranged to eject medicament through the sidewall, along a dispensing axis angled, at a non-zero angle, relative to an axis normal the sidewall at the nozzle; and
rotating the capsule proximate the tissue site of interest by ejecting the medicament along the dispensing axis according to a medicament release profile.

12. The method of claim 11, further comprising sensing one or more biological conditions in the gastrointestinal tract, and based on the sensing step, dispensing the medicament according to the medicament release profile, and/or determining or modifying the medicament release profile.

13. The method of claim 12, wherein the biological condition sensed in the sensing step is selected from a group consisting of pH level, presence or absence of bacteria or enzymes, anatomical location in the gastrointestinal tract and the presence or absence of blood.

14. The method of claim 11, wherein the capsule has first wireless communication means for receiving signals from a second wireless communication means, and further comprising, upon receipt of a signal from the second communications means, dispensing the medicament according to the medicament release profile.

15. The method of claim 11, wherein the method is employed to administer a medicament for the treatment of a disease selected from a group consisting of inflammatory bowel disease, celiac disease and intestinal cancer.

16. The method of claim 11, wherein the method is employed to administer a medicament for the treatment of Crohn's Disease or Ulcerative Colitis and the medicament is selected from a group consisting of aminosalicylates, corticosteroids, biologics, anti-coagulant medicaments, immunomodulators, probiotics and antibiotics.

17. The method of claim 11, wherein the capsule has a housing that is manufactured from at least one material selected from a group consisting of PELLETHANE 2363 polyethcrurethane series of materials, ELASTHANE polyetherurcthane, PURSIL thermoplastic silicone polyether urethane, and CARBOSIL silicone polycarbonate urethane.

18. The method of claim 11, further comprising sensing when the capsule has rotated a defined amount and stopping dispensing of the medicament.

19. The method of claim 11, wherein the control means includes a real-time clock to provide a reference for elapsed traveling time of the capsule.

20. The method of claim 11, wherein one or more of the nozzle dispensers are positioned tangentially to the surface of a housing to the capsule such that during discharge of the medicament, the capsule is caused to rotate and/or translate so as to discharge the medicament homogeneously onto one or more tissue sites of interest.

21. A capsule comprising:
a reservoir for storing a medicament; and
at least one piezoelectric droplet jet nozzle dispenser in fluid communication with the medicament reservoir, each at least one piezoelectric droplet jet nozzle dispenser including a nozzle arranged to eject medicament through a sidewall of the capsule along a dispensing axis angled, at a non-zero angle, relative to an axis normal the sidewall at the nozzle, wherein the medicament is retained by one or more micelles so as to be dispensable in accordance with a medicament release profile.

22. The capsule of claim 21, wherein the micelles aid in the absorption of medicament at one or more tissue sites of interest.

23. A capsule comprising:
a reservoir for storing one or more medicaments;
at least one piezoelectric droplet jet nozzle dispenser in fluid communication with the medicament reservoir, each at least one piezoelectric droplet jet nozzle dispenser including a nozzle arranged to eject medicament through a sidewall of the capsule along a dispensing axis angled, at a non-zero angle, relative to an axis normal the sidewall at the nozzle; and
a pressure sensor for detecting contraction pressure associated with at least one peristaltic contraction, wherein one or more medicaments are retained via said capsule so as to be dispensed in response to detection of one or more peristaltic contractions.

\* \* \* \* \*